US006387685B1

(12) United States Patent
Markham et al.

(10) Patent No.: US 6,387,685 B1
(45) Date of Patent: May 14, 2002

(54) EHV-1 VECTORS

(75) Inventors: Alexander Fred Markham; David Mark Meredith, both of Leeds (GB)

(73) Assignee: The University of Leeds, Great Britain (GB)

( * ) Notice: Subject to any disclaimer, the term of this patent is extended or adjusted under 35 U.S.C. 154(b) by 0 days.

(21) Appl. No.: 09/319,976

(22) PCT Filed: Dec. 12, 1997

(86) PCT No.: PCT/GB97/03438

§ 371 Date: Sep. 7, 1999

§ 102(e) Date: Sep. 7, 1999

(87) PCT Pub. No.: WO98/27216

PCT Pub. Date: Jun. 25, 1998

(30) Foreign Application Priority Data

Dec. 14, 1996 (GB) .............................................. 9626029

(51) Int. Cl.[7] ............................ C12N 7/00; C12N 15/00

(52) U.S. Cl. .................. 435/235.1; 435/236; 435/320.1

(58) Field of Search .............................. 435/235.1, 236, 435/320.1

(56) References Cited

U.S. PATENT DOCUMENTS 5,292,653 A 3/1994 Kit et al. ................. 435/235.1

FOREIGN PATENT DOCUMENTS

| | | |
|---|---|---|
| EP | 0 507 179 | 10/1992 |
| WO | WO 92/01045 | 1/1992 |
| WO | WO 94/00587 | 1/1994 |
| WO | WO 94/03628 | 2/1994 |
| WO | WO 95/22607 | 8/1995 |
| WO | WO 96/29421 | 9/1996 |

OTHER PUBLICATIONS

L.F. Roumillat et al., Persistent infection of a human lymphoblastoid cell line with equine herpesvirus 1, *Infect. Immun.* 24,539–544 (1979).

*Primary Examiner*—Donna Wortman
(74) *Attorney, Agent, or Firm*—Myers Bigel Sibley & Sajovec

(57) ABSTRACT

The invention relates to manipulation of equine herpes virus for use in gene therapy and in particular to modifications of the virus so that it can carry heterologous material and furthermore, preferably, be replication deficient so that the virus cannot replicate in the target tissue.

3 Claims, No Drawings

EHV-1 VECTORS

The invention relates to a method of virus manipulation; means therefor and products thereof which have particular, but not exclusive, application in gene therapy/vaccine development.

Human gene therapy virus vectors constructed to date are derived from adenovirus, retrovirus, parvovirus and herpesvirus families. With the exception of retroviruses, all have been derived from viruses originally isolated from humans. In nearly every case the vectors used in both ex and in vivo work have been derived from virus mutants originally created to study gene function, rather than to act as gene delivery systems. A virus-derived vector capable of efficient gene delivery to human epithelial mucosal cells would have a wide range of uses in human gene therapy, for example delivery of a correct copy of the cystic fibrosis transmembrane regulator protein to the lung or a range of human tumour suppressor genes to tumours of the lung and colon or additionally as a vaccine delivery vehicle to induce muscosal immunity.

Although adenoviruses have proved to be popular because of ease of growth of stocks to high titre, they have many problems, as viruses which are replication incompetent in cell culture have caused tissue damage and respiratory disease in patients treated with such vectors (1,2). Furthermore, adenovirus vectors with further gene deletions to express proteins are in development, but these grow less well in culture than the original E1A (a gene essential for adenovirus replication in tissue culture) deletion mutants (3), which suggests production problems in the longer term. The compact nature of the adenovirus genome, in which many of the early regulatory genes are components of overlapping gene clusters, which are differentially spliced, makes it difficult to delete the coding region of single transcripts (4). Furthermore, adenoviruses have a packaging constraint which prevents the introduction of heterologous DNA sequences >8Kbp. One of the biggest problems with adenoviruses resides in the lack of information on virus gene function in pathogenesis (5). It is very difficult to predict, at present, which genes might be deleted in order to create a completely replication defective virus in vivo. In addition, one of the major structural components of adenoviruses, the fibre, responsible for cell attachment, can itself cause a cytopathic effect (6).

Retrovirus vectors have, for the most part, been derived from murine viruses which have a broad host range (amphotropic). This group of virus vectors has been the most extensively developed, mainly because they fulfill many of the simplistic criteria needed in a vector for gene therapy. They can be made totally replication incompetent, integrate into host cell chromosomes and are inherited in a dividing cell population. Theoretically, this random chromosomal integration may have pathological consequences. Their major disadvantage is that they have a limited packaging capacity and only vectors being developed from HIV have the potential to infect and integrate their genetic material into post-mitotic cells. Furthermore, these vectors have to be produced through DNA transfection (7), and high titre stocks are, at present, impossible to produce.

Parvovirus vectors have some of the same advantages as retroviruses through their ability to integrate into chromosomes and thus the transferred gene may be inherited in daughter cells (8). Their main disadvantage is that it is impossible to produce high titre stocks and the genome has a packaging capacity which is significantly less than that of retroviruses (9).

Herpesvirus vector development to date has concentrated on derivatives of the common human pathogen herpes simplex virus (HSV). The advantage of using this virus is that it is the most intensively studied of all the herpesviruses. The sequence of the virus genome has been determined, there is a wide range of well characterised virus mutants available and transcriptional control processes are well understood. In addition, pathogenicity of the virus and the host immune response have been intensively studied for many years. It is clear, however that although it is possible to delete genes encoding proteins involved in neuropathogenicity (10) and immediate-early transcriptional activators, (11) or to inactivate the virion-associated activator of immediate-early genes (12), such mutant viruses are difficult to produce as high titre stocks and in some cases have an unacceptable reversion frequency, through their propagation in helper cell lines (11). Encouraging results have been obtained with neuronal expression of heterologous genes in animal models, and it is likely that further disabled vectors will be derived (13, 14, 15). The likely problem with HSV vectors is the innate immune response present in the majority of the population; we would predict that HSV vectors will suffer the same problem as those derived from human adenoviruses, when delivered to an immunologically competent site.

Other herpesviruses might be more appropriate to develop as vectors for human tissues. For example one might use the $\alpha$-herpesviruses. This group consists of a large number of viruses probably equal to a multiple of the number of susceptible species given that typically 2–3 viruses infect each of the known susceptible species. Thus $\alpha$-herpesviruses have long been known to have a very broad cell tropism. For instance, HSV can infect and replicate in cells derived from species as diverse as *bovidae* and *muridae*. Certain viruses from these, species can, conversely, infect human cells. It is apparent that failure in the replication of viruses infecting cells of a different species than the usual host is often due to transcriptional blocks (16).

This might therefore offer an immediate advantage in the development of a gene therapy vector. An appropriate virus might be chosen which naturally cannot replicate in human cells, but is able to deliver nucleic acid to the cell in an efficient manner.

EHV-1 is naturally a respiratory pathogen of horses (17). It also has the capability of causing abortion in pregnant mares. The virus replicates readily in cells from a wide variety of species including hamster, mouse and rabbit. In addition, we have now shown that the virus is able to replicate in human and primate cells.

We have, serendipitously, chosen this virus for interspecies gene therapy despite the large number of possible candidates and the prevailing convention of using intraspecies viruses for gene therapy.

EHV-1 has been chosen as although we have shown the virus is capable of infecting human cells (18) of different lineages in vitro, it does not appear to infect humans in vivo. Surveys have been carried out in populations of potentially susceptible individuals, yet there is no evidence of any transmission of this virus to humans (17). No seroconversion of a human has ever been reported. As this virus is a respiratory pathogen it offers the potential of being able to deliver genes to the respiratory tract as well as other mucosal surfaces of humans.

EHV-1 is, as far as can be ascertained, apathogenic for man. There are no published studies regarding seroconversion for humans whilst working with the virus, and workers in the field who have looked for a specific anti-EHV-1 response have not been able to detect any evidence that the virus replicates in human tissues studied. There is a well-established animal model for studying respiratory disease caused by EHV-1. Mice are dosed with suspensions of virus intranasally, subsequent to which they develop a transient febrile respiratory disease, during which time virus may be detected in lung tissue. It has already been shown that deletion of certain genes, non-essential for replication in tissue culture make the virus essentially apathogenic in mice. The ability to create a gene delivery vehicle which is not a human pathogen, unable to replicate in vivo but able to infect respiratory and other mucosal epithelium is obviously attractive, as the viruses developed to date for such purposes either have to be injected directly at the site of disease (retroviruses), or are likely to cause pathological respiratory infections (adenoviruses).

We believe that vectors derived from EHV-1 offer a wide range of opportunities to target mucosal cells both with protective and/or therapeutic genes or fragments thereof thus offering the unique opportunity to deliver a stably-expressing, extrachromosomal element, to a specific cell population. Additionally, and most importantly, by employing vectors derived from a virus which is apathogenic for man an immediate destruction of the agent by the patients immune response will be avoided.

It is therefore a first object of the invention to provide a gene delivery system/vaccine derived from a non-human apathogenic virus.

It is therefore a yet further object of the invention to provide a gene delivery system/vaccine to deliver at least a part of at least one preselected gene to a selected cell population.

In its broadest aspect the invention concerns the use of EHV to deliver heterologous genetic material to a specific human cell population and ideally to mucosal cells.

According to a first aspect of the invention there is provided an equine herpes virus adapted to receive genetic material encoding at least part of a preselected protein for use in delivering said protein to a human cell population and preferably a specific cell population and ideally to normal or malignant muscosal cells.

In a preferred embodiment of the invention said equine herpes virus ideally includes at least a part of a gene encoding a specific protein.

Ideally said gene, or part thereof, codes for either one or more of the following proteins p53, Cystic Fibrosis Transmembrane Regulator (CFTR), adematous polyposis coli (APC), 1 antitrypsin, FKBP-rapamycin associated protein (FRAP) or cytosine deaminase.

In a yet further preferred embodiment of the invention said equine herpes virus lacks or has at least one mutation in at least one gene responsible for, or associated with replication such that the gene product is lacking or is nonfunctional so that the virus cannot replicate.

Further, or in addition, EHV may be suitably modified in order to facilitate its use as an agent for effecting gene transfer. For example, non essential genes may be deleted in order to facilitate the delivery of large amounts of heterologous DNA that is in the order of more than 10 and preferably 50' kilobases. In addition, or instead, EHV may be modified so as to render it safe and controllable, for example, genes encoding transcriptional control proteins may be mutated and/or deleted so as to disable the replication cycle of the virus.

Thus in a further preferred embodiment of the invention there is provided said EHV, as described above, modified so that genes relating to non-essential gene 9 and/or essential gene 12 and/or non-essential gene 28 and/or non-essential gene 38 and/or non-essential gene 52 and/or non-essential gene 49 are mutated and/or deleted, and/or disabled.

According to a further aspect of the invention there is provided a vector adapted to introduce heterologous DNA into EHV wherein said heterologous DNA encodes at least part of a protein to be delivered to a specified cell population. Ideally said vector is a plasmid construct and more ideally is provided with a marker gene.

According to a yet further aspect of the invention there is provided an equine herpes virus including heterologous DNA encoding at least part of a protein to be delivered to a mucosal cell population, wherein said protein comprises at least part of one or more of the following proteins p53 and/or CFTR and/or APC and/or 1 antitrypsin and/or FRAP and/or cytosine deaminase.

An embodiment of the invention will now be described by way of example only with reference to the following materials and methods:

EXPERIMENTAL APPROACH

Generation of EHV-1 Recombinant Viruses Deleted in Individual Genes

Two methods have been used, depending on the type of virus mutant under construction. Viruses with deletions in non-essential genes have been produced using co-transfection of infectious virus DNA and plasmid constructs which contain the beta-galactosidase gene under the control of a strong heterologous promoter, in the presence of the transfection reagent DOTAP. This was inserted in a manner which on recombination deleted part of the coding sequence of the appropriate virus gene. Replication of the virus DNA along with the plasmid DNA allowed homologous recombination to occur between the appropriate strands of DNA and viruses have been produced which contain the engineered DNA fragment in place of normal genes. These viruses were isolated through plaque purification and their genetic integrity confirmed by Southern blotting.

Virus deletants which contained disruptions in genes essential for virus replication in culture were isolated utilising helper cell lines. Helper cell lines were produced by co-transfecting a clone of the appropriate gene under the control of either its own or a heterologous promoter, along with a selectable marker gene, neomycin phosphotransferase. Stable cell lines, resistant to the antibiotic G418 (expressing neomycin phosphotransferase), were tested for their ability to express each virus gene using either RT-PCR or antibodies specific for the gene product. Recombinant viruses were propagated on these cell lines, which provided the essential gene in trans.

Deletion in Essential Gene 12 (Virion-associated Transcriptional Activator)

The opening reading frame lies between nucleotides 13,505 and 14,944 in the published Ab1 EHV strain sequence and comprises 479 amino acids. The gene has been cloned from virus DNA using PCR primers flanking the open reading frame, to construct plasmid pBKRSV12 (deposited with the National Collection of industrial and Marine Bacteria Limited (NCIMB), 23 St.Machan Drive, Aberdeen, AB2 1RY; deposition number 40913). This plasmid contains the RSVLTR promoter and thus is capable of expressing the ORF12 reading frame. Digestion of this plasmid with restriction endonucleases Bgl II and Xho 1 removes a 670 bp fragment The remaining plasmid was purified by gel electrophoresis and relegated This was co-transfected with infectious virus DNA into cells expressing gene 12 (see below) and progeny virus containing the delection were detected by PCR and Southern blotting using standard techniques. of Industrial and Marine Bacteria Limited (NCIMB), 23 St.Machan Drive, Aberdeen, AB2 IRY; deposition number). This plasmid contains the RSVLTR promoter and thus is capable of expressing the ORF 12 reading frame. Digestion of this plasmid with restriction endonucleases Bg1 II and Xho 1 removes a 670 bp fragment. The remaining plasmid was purified by gel electrophoresis and religated to create plasmid pBKK412 (deposited with the NCIMB at the above address; deposition number). This was co-transfected with infectious virus DNA into cells expressing gene 12 (see below) and progeny virus containing the deletion were detected by PCR and Southern blotting using standard techniques.

$10^6$BHK cells were transfected with 2 µg pDM312 in a solution of DOTAP in sterile PBS. After 48 h, cells were detached from the culture vessel with trypsin, resuspended in fresh culture medium and plated out at $10^4$ cells per 10 cm diameter culture dish in medium containing 800 µg/ml G418. Drug resistant colonies were selected after 2 weeks, and assayed for expression of the EHV gene by RT-PCR. Positive clones were expanded and used as the helper cell lines for propagation of the gene 12-deleted virus.

Deletion in Non-essential Gene 28 (Non-structural Protein of Unknown Function)

The open reading frame of gene 28 lies between nucleotides 48,763 and 50625 of the published virus genome sequence. The complete open reading frame was amplified using PCR and cloned into plasmid pGEX-2T to generate pAP301. This was then digested with restriction endonucleases Sst II and Cla1 to delete 645 bp of coding sequence. The beta-galactosidase gene under control of the CMV IE3 promoter was inserted at this site to produce plasmid pAP302. This construct was co-transfected into BHK cells with infectious EHV-1 DNA, virus progeny collected and plated out onto BHK cells for plaque purification in the presence of X-gal indicator. Blue plaques were picked and subjected to multiple rounds of plaque purification to generate pure recombinant virus.

Deletion in Non-essential Gene 38 (Thymidine Kinase)

The open reading frame of gene 38 lies between nucleotides 69,910 and 70,968 of the published virus genome sequence and encodes a 352 amino acid protein. The complete open reading frame was amplified using PCR and cloned into plasmid LITMUS28 to generate pDM331. This was then digested with restriction endonucleases Xcm1 and Kas1 to delete 504 bp of coding sequence. The beta-galactosidase gene under control of the CMV IE3 promoter was inserted at this site to produce plasmid pDM332. This construct was co-transfected into BHK cells with infectious EHV-1 DNA, virus progeny collected and plated out onto BHK cells for plaque purification in the presence of X-gal indicator. Blue plaques were picked and subjected to multiple rounds of plaque purification to generate pure recombinant virus.

Deletion in Non-essential Gene 52 (Glycoprotein M)

The open reading frame was amplified using PCR and cloned into plasmid pSP72 to generate pAP402. This was then digested with restriction endonucleases Xma III and Msc 1 to delete 530 bp of coding sequence. The beta-galactosidase gene under control of the CMV IE3 promoter was inserted at this site to produce plasmid pAP403. This construct was co-transfected into BHK cells with infectious EHV-1 DNA, virus progeny collected and plated out onto BHK cells for plaque purification in the presence of X-gal indicator. Blue plaques were picked and subjected to multiple rounds of plaque purification to generate pure recombinant virus.

Deletion in Non-essential Gene 49 (Virion Protein Kinase)

The open reading frame was amplified using PCR and cloned into plasmid pUC18 and termed pORF49. This was digested with restriction endonuclease HincII and a cassette containing the β-galactosidase gene under the control of the CMV promoter was inserted trough blunt end ligation to generate pUCORF49LacZ (deposited at the NCIMB at the above address; deposition number 40912). This construct was co-transfected into BHK cells with infectious EHV-1 DNA, virus progeny collected and plated out onto BHK cells for plaque purification in the presence of X-gal indicator. Blue plaques were picked and subjected to multiple rounds of plaque purification to generate pure recombinant virus.

Deletion in Non-essential Gene 9 (dUTPase)

The open reading frame was amplified using PCR and cloned into pUC18 and termed pORF9. This was digested with restriction endonuclease EcoRV and a cassette containing the β-galactosidase gene under the control of the CMV promoter was inserted through blunt end ligation to generate pUCORF9LacZ (deposited at the NCIMB at the above address; deposition number 40911). This construct was co-transfected with infectious virus DNA, virus progeny collected and plated out onto BHK cells for plaque purification in the presence of X-gal. Blue plaques were picked and subjected to multiple rounds of plaque purification to generate pure recombinant virus.

REFERENCES

1. Rich, D. P., Couture, L. A., Cardoza, L. M., Guiggio, V. M., Armentano, D., Espino, P. C., Hehir, K., Welsh, M. J., Smith, A. E. and Gregory, R. J. (1993). Development and analysis of recombinant adenoviruses for gene therapy of cystic fibrosis. *Hum. Gene. Ther.* 4, 461–467.
2. Crystal, R. G., McElvaney, N. G., Rosenfeld, M. A., Chu, C., Mastrangeli, A., Hay, J. G., Brody, S. L., Jaffe, H. A., Eissa, N. T. and Danel, C. (1994). Administration of an adenovirus containing the human CFTR cDNA to the respiratory tract of individuals with cystic fibrosis. *Nature Genet*. 8, 42–51.
3. Weinberg, D. H. and Ketner, G. (1986). Adenoviral early region 4 is required for efficient viral DNA replication and for late gene expression. *J. Virol.* 57, 833–838.
4. Hemstrom, C., Nordqvist, K., Pettersson, U., and Vitanen, A. (1988). Gene product of region E4 of adenovirus 5 modulates accumulation of certain viral polypeptides. *J. Virol.* 62, 3258–3264.
5. Schenk, T. (1995). *The adenoviridae in "Virology"*, ed. Fields, 3rd edition, Raven Press, N.Y.
6. Defer, C., Belin, M-T., Caillet-Boullin, M-L and Boulanger, P. (1990). Human adenovirus-host cell interactions: comparative study with members of subgroups B and C. *J. Virol*. 64, 3661–3673.
7. Soneoka, Y., Cannon, P. M., Ramsdale, E E, Griffiths, J. C., Romano, G., Kingsman, S. and Kingsman, A. (1995).

A transient three-plasmid expression system for the production of high titre retroviruses. *Nucl Acid Res.* 23, 628–633.

8. Cheung, A., Hoggan, M., Hauswirth, W. and Berns, K. I. (1980). Integration of the adeno-associated virus genome into cellular DNA in latently infected Detroit 6 cells. *J. Virol.* 33, 739–748.

9. Wang, X., Ponnazhagan, S. and Srivastava, A. (1996). Rescue and replication of adeno-associated virus type 2 as well as vector DNA sequences from recombinant plasmids containing deletions in the viral inverted terminal repeats: selective encapsidation of viral genomes in progeny virions. *J. Virol.* 70, 1668–1677.

10. Chou, J., Kern, E. R., Whiteley, R. J., and Roizman, B. (1990). Mapping of the herpes simplex virus 1 neurovirulence gene to 34.5, a gene nonessential for growth in culture. *Science.* 250, 1262–1265.

11. DeLuca, N. A., McCarthy, A. M. and Schaffer, P. A. (1985). Isolation and characterisation of deletion mutants of herpes simplex virus type 1 in gene encoding immediate-early regulatory protein ICP4. *J. Virol.* 56, 558–570.

12. Weinheimer, S. P., Boyd, B. A., Durham, S. K., Resnick, J. L. and O'Bole, D. R. (1992). Deletion of the VP16 open reading frame of herpes simplex virus type 1. *J. Virol.* 66, 258–269.

13. Randazzo, B. P., Keasari, S., Gesser, R., Alsop, D., Ford, J. C., Brown, S. M., Maclain, A. and Fraser, N. (1995). Treatment of experimental murine melanoma with a neuroattenutated herpes simplex virus 1 mutant. *Virology.* 211, 94–101.

14. Kennedy, P. G. E. and Steiner, I. (1993). The use of herpes simplex virus vectors for gene therapy in neurological disease. *Quat. J. Med.* 86, 697–702.

15. Lu, B., Gupta, S. and Federoff, H. (1995). Ex vivo hepatic gene transfer using a defective herpes simplex virus-1 vector. *Hepatology.* 21, 752–759.

16. Sears, A. and Roizman, B. (1995). *The herpes simplex viruses* in "Virology", ed. Fields, 3rd edition, Raven Press, N.Y.

17. Allen, G. P. and Bryans, J. T. (1986). Molecular epizooitology, pathogenesis and prophylaxis of equine herpesvirus 1 infections. Prog. Vet. Micro. Immunol. 2, 78–144.

18. Griffiths, J. G., Whitehouse, A. and Meredith, D. M., unpublished data.

We claim:

1. A recombinant EHV-1 wherein gene 12 has been deleted.

2. The recombinant EHV-1 of claim 1, wherein said EHV-1 further comprises a deletion in an additional gene.

3. The recombinant EHV-1 of claim 2, wherein said additional gene is selected from the group consisting of gene 9, gene 28, gene 52, and gene 49.

* * * * *